United States Patent
Sharonov

(10) Patent No.: US 9,351,643 B2
(45) Date of Patent: May 31, 2016

(54) SYSTEMS AND METHODS FOR OPTICAL MEASUREMENT FOR IN-SITU SURGICAL APPLICATIONS

(71) Applicant: Covidien LP, Mansfield, MA (US)

(72) Inventor: Alexey Sharonov, Bethany, CT (US)

(73) Assignee: Covidien LP, Mansfield, MA (US)

( * ) Notice: Subject to any disclaimer, the term of this patent is extended or adjusted under 35 U.S.C. 154(b) by 64 days.

(21) Appl. No.: 14/164,550

(22) Filed: Jan. 27, 2014

(65) Prior Publication Data

US 2014/0276097 A1    Sep. 18, 2014

Related U.S. Application Data

(60) Provisional application No. 61/777,000, filed on Mar. 12, 2013.

(51) Int. Cl.
| | |
|---|---|
| *A61B 5/00* | (2006.01) |
| *A61B 18/22* | (2006.01) |
| *A61B 19/00* | (2006.01) |
| *A61B 17/00* | (2006.01) |

(Continued)

(52) U.S. Cl.
CPC ............... *A61B 5/0059* (2013.01); *A61B 1/00* (2013.01); *A61B 5/1076* (2013.01); *A61B 17/00234* (2013.01); *A61B 18/22* (2013.01); *A61B 19/46* (2013.01); *A61B 19/5202* (2013.01); *G01B 11/02* (2013.01); *G01B 11/2513* (2013.01); *A61B 2019/461* (2013.01)

(58) Field of Classification Search
CPC .. A61B 17/00234; A61B 18/22; A61B 19/46; A61B 19/5202; A61B 1/00; A61B 2019/461; A61B 5/0059; A61B 5/1076; G01B 11/02; G01B 11/2513

See application file for complete search history.

(56) References Cited

U.S. PATENT DOCUMENTS

| | | |
|---|---|---|
| 3,817,635 A | 6/1974 | Kawahara |
| 3,819,267 A | 6/1974 | Kawahara |

(Continued)

FOREIGN PATENT DOCUMENTS

| | | |
|---|---|---|
| DE | 36 29 435 A1 | 3/1987 |
| EP | 0 403 399 A2 | 12/1990 |

(Continued)

OTHER PUBLICATIONS

Extended European Search Report dated Jun. 12, 2014 for EP 14 15 8762.

(Continued)

*Primary Examiner* — Michael Rozanski

(57) ABSTRACT

A system and method is presented for performing optical measurements, including a light source configured to emit a light beam, a first pattern generator defining a first longitudinal axis and configured to project a first generated pattern, and a second pattern generator defining a second longitudinal axis and configured to project a second generated pattern. The first and second generated patterns have different angular divergency. The first pattern generator is a diffractive circle pattern generator, whereas the second pattern generator is a diffractive cross pattern generator. Adjustment of the first and second generated patterns with respect to each other cause the system to serve as an optical ruler for performing the optical measurements when the first and second generate patterns overlap or coincide with each other at certain points.

29 Claims, 8 Drawing Sheets

(51) Int. Cl.
  *A61B 1/00* (2006.01)
  *A61B 5/107* (2006.01)
  *G01B 11/02* (2006.01)
  *G01B 11/25* (2006.01)

(56) References Cited

U.S. PATENT DOCUMENTS

| | | |
|---|---|---|
| 3,943,361 A | 3/1976 | Miller |
| 4,281,931 A | 8/1981 | Chikama |
| 4,660,982 A | 4/1987 | Okada |
| 4,702,229 A | 10/1987 | Zobel |
| 4,834,070 A | 5/1989 | Saitou |
| 4,902,123 A | 2/1990 | Yoder, Jr. |
| 4,958,932 A | 9/1990 | Kegelman et al. |
| 4,980,763 A | 12/1990 | Lia |
| 4,986,262 A | 1/1991 | Saito |
| 5,090,400 A | 2/1992 | Saito |
| 5,285,785 A | 2/1994 | Meyer |
| 5,558,666 A | 9/1996 | Dewey et al. |
| 5,669,871 A | 9/1997 | Sakiyama |
| 5,808,813 A | 9/1998 | Lucey et al. |
| 6,063,023 A | 5/2000 | Sakiyama et al. |
| 6,070,583 A | 6/2000 | Perelman et al. |
| 6,360,012 B1 | 3/2002 | Kreuzer |
| 6,451,010 B1 | 9/2002 | Angeley |
| 6,482,148 B1 | 11/2002 | Luke |
| 6,542,763 B1 | 4/2003 | Yamashita et al. |
| 6,611,698 B1 | 8/2003 | Yamashita et al. |
| 6,741,338 B2 | 5/2004 | McArthur et al. |
| 6,945,930 B2 | 9/2005 | Yokota |
| 7,310,431 B2 | 12/2007 | Gokturk et al. |
| 7,486,805 B2 | 2/2009 | Krattiger |
| 7,532,311 B2 | 5/2009 | Henderson et al. |
| 7,556,599 B2 | 7/2009 | Rovegno |
| 7,720,532 B2 | 5/2010 | Hashimshony et al. |
| 7,812,968 B2 | 10/2010 | Bendall et al. |
| 7,862,555 B2 | 1/2011 | Chan et al. |
| 2005/0237423 A1 | 10/2005 | Nilson et al. |
| 2006/0092418 A1 | 5/2006 | Xu et al. |
| 2009/0054767 A1 | 2/2009 | Telischak et al. |
| 2009/0270682 A1 | 10/2009 | Visser |
| 2010/0020333 A1 | 1/2010 | Kunz et al. |
| 2010/0046004 A1 | 2/2010 | Lee et al. |

FOREIGN PATENT DOCUMENTS

| | | |
|---|---|---|
| EP | 1 480 067 A1 | 11/2004 |
| EP | 2 106 748 A1 | 10/2009 |
| EP | 2 524 650 A2 | 11/2012 |
| WO | WO 00/08415 A1 | 2/2000 |
| WO | WO 2005/013814 A | 2/2005 |

OTHER PUBLICATIONS

Extended European Search Report dated Sep. 16, 2013 for EP 12 19 0097.
Extended European Search Report dated Mar. 4, 2013 for EP 12 19 0094.
Extended European Search Report dated Mar. 26, 2013 for EP 12 16 8466.

SYSTEMS AND METHODS FOR OPTICAL MEASUREMENT FOR IN-SITU SURGICAL APPLICATIONS

CROSS-REFERENCE TO RELATED APPLICATIONS

This application claims the benefit of and priority to U.S. Provisional Patent Application No. 61/777,000, filed Mar. 12, 2013, the entire disclosure of which is incorporated by reference herein.

BACKGROUND

1. Technical Field

The present disclosure relates to a system and method for measuring a dimension of a target site. More particularly, the present disclosure relates to a system and method of projecting an image for use in measuring a dimension of a target site.

2. Background of the Related Art

Minimally invasive surgery, e.g., laparoscopic, endoscopic, and thoroscopic surgery, has many advantages over traditional open surgeries. In particular, minimally invasive surgery eliminates the need for a large incision, thereby reducing discomfort, recovery time, and many of the deleterious side effects associated with traditional open surgery.

The minimally invasive surgeries are performed through small openings in a patient's skin. These openings may be incisions in the skin or may be naturally occurring body orifices (e.g., mouth, anus, or vagina). In general, insufflation gas is used to enlarge the area surrounding the target surgical site to create a larger, more accessible work area.

During minimally invasive procedures, it is often difficult for a surgeon to determine sizes of various organs, tissues, and other structures in a surgical site. Various in-situ surgical metrology methods exist for measurement in a surgical site. Such methods require many moving parts and projection images that change size and/or focus quickly as projectors move in or out of a surface of projection. Thus, a continuing need exists for in-situ surgical metrology methods that operate with a stable focus and no moving parts.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

A system for performing optical measurements is presented. The system includes a light source configured to emit a light beam, a first pattern generator defining a first longitudinal axis and configured to project a first generated pattern, and a second pattern generator defining a second longitudinal axis and configured to project a second generated pattern. The first and second generated patterns have different angular divergency.

In an exemplary embodiment, the light source is a laser.

In another exemplary embodiment, the first pattern generator is a diffractive circle pattern generator, whereas the second pattern generator is a diffractive cross pattern generator.

In yet another exemplary embodiment, the first pattern generator is located between the light source and the second pattern generator.

In an exemplary embodiment, the first pattern generator is positioned at a first distance with respect to the light source and the second pattern generator is positioned at a second distance with respect to the light source, the second distance being greater than the first distance.

In another exemplary embodiment, the first and second generated patterns are projected onto a target site in an overlapping manner.

In yet another exemplary embodiment, the first generated pattern is a circle and the second generated pattern is a cross-hair that is adjusted with respect to the circle based on the distance of the system relative to the target site. Additionally, adjustment of the first and second generated patterns with respect to each other cause the system to serve as an optical ruler for performing the optical measurements when the first and second generated patterns overlap.

In an exemplary embodiment, the first and second longitudinal axes are parallel to each other and are offset from each other by a predetermined distance to create the different angular divergency of the first and second generated patterns.

Moreover, the system is configured to be mounted on a surgical device.

In another embodiment, a surgical instrument is presented including a handle portion, a body portion extending distally from the handle portion and defining a longitudinal axis, an end effector assembly disposed at a distal end of the body portion and an optical measurement system. The optical measurement system includes a beam delivery element for projecting a beam along an illumination path and onto a plane and first and second diffractive optical elements positioned along the illumination path of the beam delivery device, the first and second diffractive optical elements configured to project first and second generated patterns, in an overlapping manner, onto the plane, and having different angular divergency.

In an embodiment, the beam delivery element is a laser.

In another embodiment, the first diffractive optical element is a diffractive circle pattern generator and the second diffractive optical element is a diffractive cross pattern generator.

In yet another exemplary embodiment, the first diffractive optical element is located between the light source and the second diffractive optical element.

In another embodiment, the first generated pattern is a circle and the second generated pattern is a cross-hair that is adjusted with respect to the circle based on the distance of the optical measurement system relative to the target site. Additionally, adjustment of the first and second generated patterns with respect to each other cause the optical measurement system to serve as an optical ruler for performing optical measurements when the first and second generated patterns overlap.

In another embodiment, a method of performing optical measurements is presented. The method includes the steps of mounting an optical measurement system onto a surgical instrument, projecting a beam along an illumination path and onto a plane, via a beam delivery element, positioning first and second diffractive optical elements along the illumination path, and projecting first and second generated patterns, in an overlapping manner, onto the plane, and having different angular divergency, via the first and second diffractive optical elements.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The above and other aspects, features, and advantages of the present disclosure will become more apparent in light of the following detailed description when taken in conjunction with the accompanying drawings in which.

Figure 1:
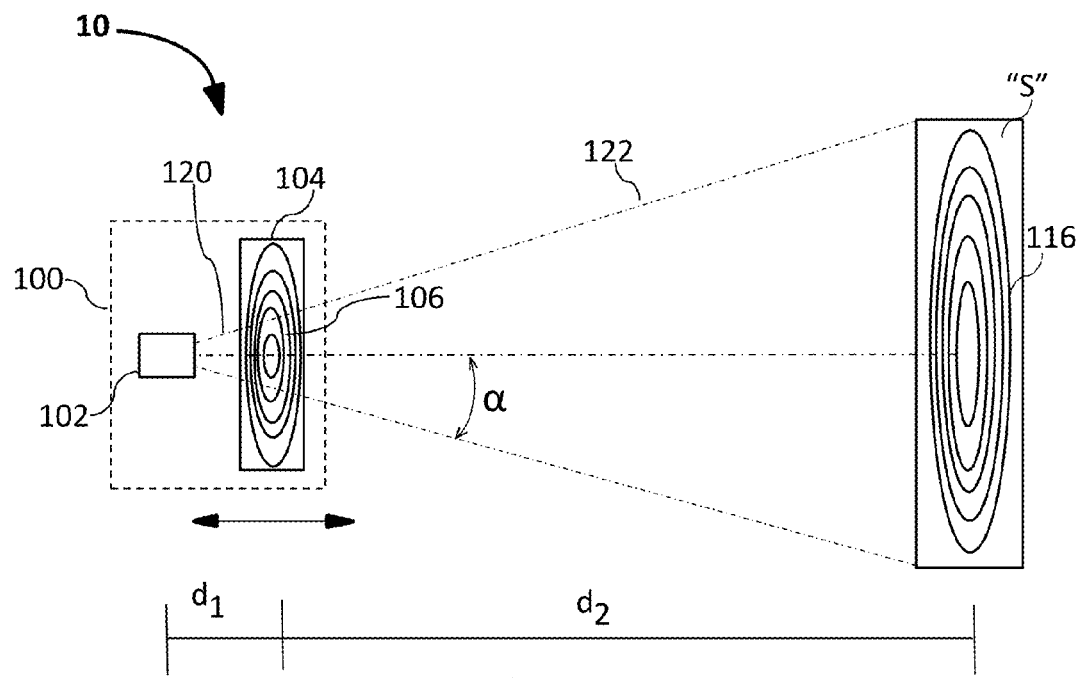
FIG. 1 is a side, schematic view of a metrology system.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is farther away from the user. The term "clinician" refers to any medical professional (i.e., doctor, surgeon, nurse, or the like) performing a medical procedure involving the use of embodiments described herein.

The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

As seen in FIG. 1, a metrology system 10 includes a point source projector 100 having a point source light emitter 102 and a mask 104. Mask 104 is at a distance, $d_1$, from point source light emitter 102 and a distance, $d_2$, from a target site "S." Mask 104 is semi-transparent and has a substantially opaque mask pattern 106 thereon. Mask pattern 106 has markings of known distances therebetween. For example, mask pattern 106 may be a series of uniformly spaced concentric circles. Mask 104 may be translatable toward or away from point source light emitter 102.

Point source light emitter 102 emits a light beam 120 therefrom. Light beam 120 approximates a point at point source light emitter 102 and conically diverges therefrom at an angle α. Point source light emitter 102 may be any device capable of emitting light from a narrow point, such as a laser diode or an LED. Light beam 120 is partially blocked by mask pattern 106 upon incidence with mask 104. An unblocked portion 122 of light beam 120 continues past mask 104 to reach target site "S." Unblocked portion 122 creates a magnified pattern 116 on target site "S." Magnified pattern 116 is magnified from mask pattern 106 according to formula: $M=1+d_2/d_1$, where, M, is a magnification factor between mask pattern 106 and magnified pattern 116. A translation of mask 104 or point source projector 100 away from target site "S" increases magnification factor M. A translation of mask 104 or point source projector 100 toward target site "S" decreases magnification factor M. Magnified pattern 116 retains a substantially sharp focus as mask 104 and/or point source projector 100 is translated.

Figure 2:
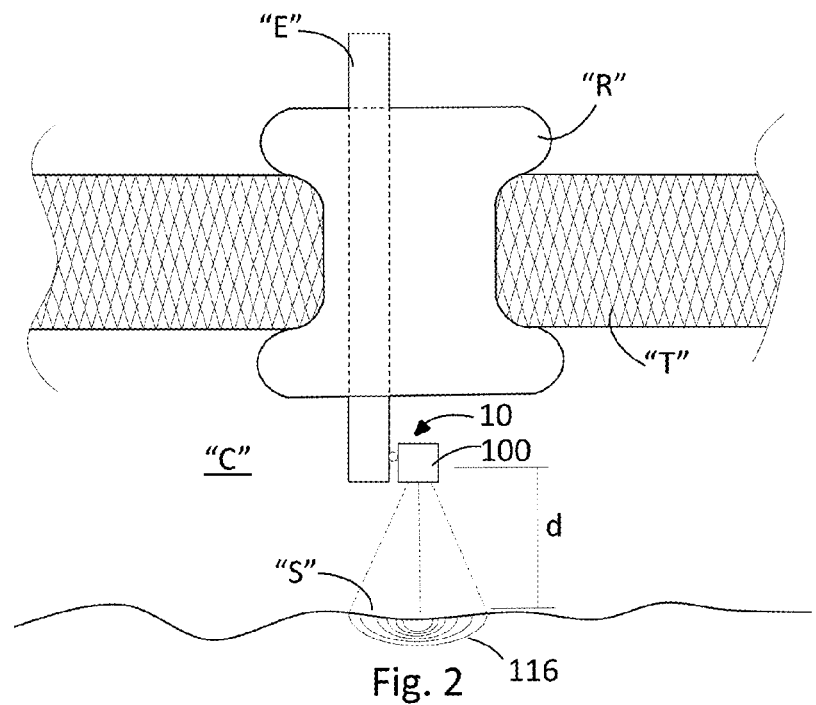
FIG. 2 is a side, perspective view of a method of use of the metrology system of FIG. 1.

A method of use of metrology system 10 is depicted in FIG. 2. Metrology system 10 is attached to a distal end of an endoscope "E." Endoscope "E" is inserted into a body cavity "C" through an opening in a tissue "T." Endoscope "E" may be inserted through a seal anchor "R" positioned within the opening in tissue "T." Endoscope "E" is inserted through a port in seal anchor "R" that is expanded to a width greater than a maximum combined width of endoscope "E" and point source projector 100. Once the distal end of endoscope "E" is distal to seal anchor "R," the port resiliently compresses to form a substantially airtight seal around endoscope "E." Point source projector 100 is translated distally toward target site "S" until point source projector 100 arrives at a known distance, d, from target site "S." The arrival of point source projector 100 at distance, d, may be determined through any appropriate means, such as triangulation. Distance, $d_1$, may be fixed prior to insertion of endoscope "E." Alternatively, endoscope "E" may include a mechanism, such as a rotatable knob (not shown), for altering distance $d_1$. Distance, $d_2$, is calculated by subtracting distance, $d_1$, from distance d. Distance, $d_1$, and distance, $d_2$, may then be used to calculate magnification factor M.

Point source projector 100 projects magnified pattern 116 onto target site "S." A clinician may observe magnified pattern 116 through endoscope "E." A dimension of target site "S" is measured by visually inspecting and counting a number, n, of uniformly spaced markings appearing along the dimension of target site "S." The number, n, of uniformly spaced markings is multiplied by a uniform distance between individual markings of pattern 116. The uniform distance between individual markings of pattern 116 is calculated by multiplying a uniform distance, $d_k$, between individual markings of mask 104 by magnification factor M. Thus, a measure of the dimension of target site "S" is calculated according to formula: $x=nMd_k$, where, x, is the measure of the dimension.

Figure 3:
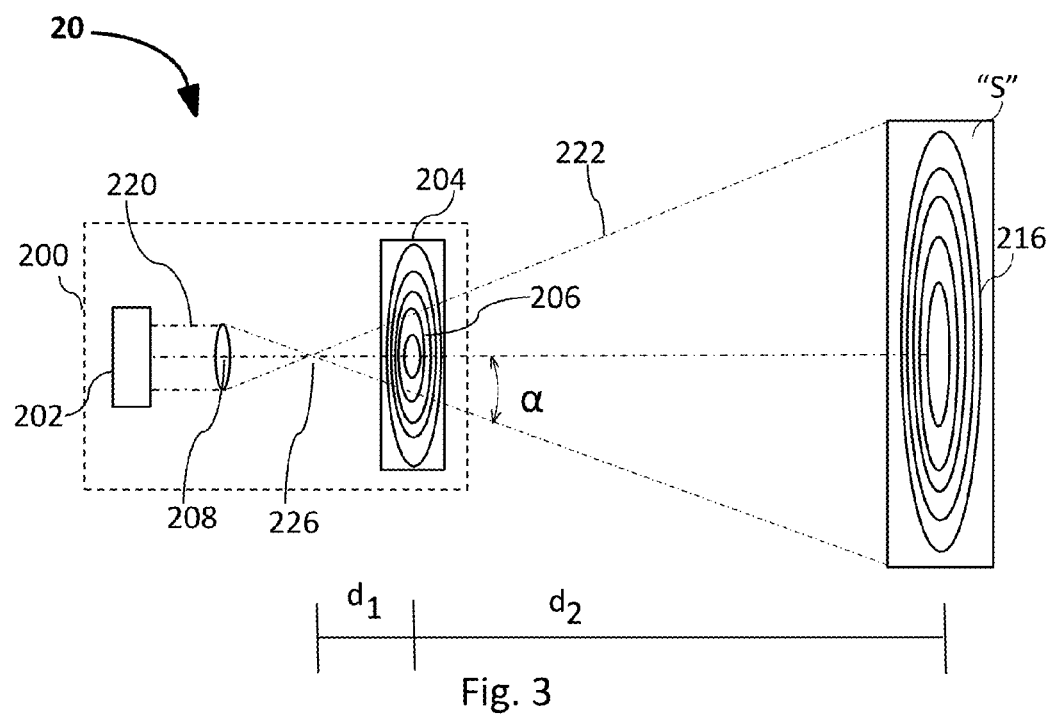
FIG. 3 is a side, schematic view of a metrology system, according to another embodiment.

Turning to FIG. 3, a metrology system in accordance with an alternate embodiment of the present disclosure is generally designated as 20. Metrology system 20 is similar to metrology system 10 and thus will only be discussed as necessary to identify the differences in construction and operation thereof.

Metrology system 20 includes a point source projector 200 having a light source 202, a mask 204, and a lens 208. Mask 204 has a mask pattern 206. Light source 202 emits a light beam 220 toward lens 208. Lens 208 is a converging lens that focuses light beam 220 into a point 226. Point 226 is a distance $d_1$ away from mask 204. Light beam 220 diverges at an angle, α, from point 226 and is partially blocked by mask 204. An unblocked beam 222 passes through mask 204 and travels a distance, $d_2$, to a target site "S" to form a magnified pattern 216 thereon.

Figure 4:
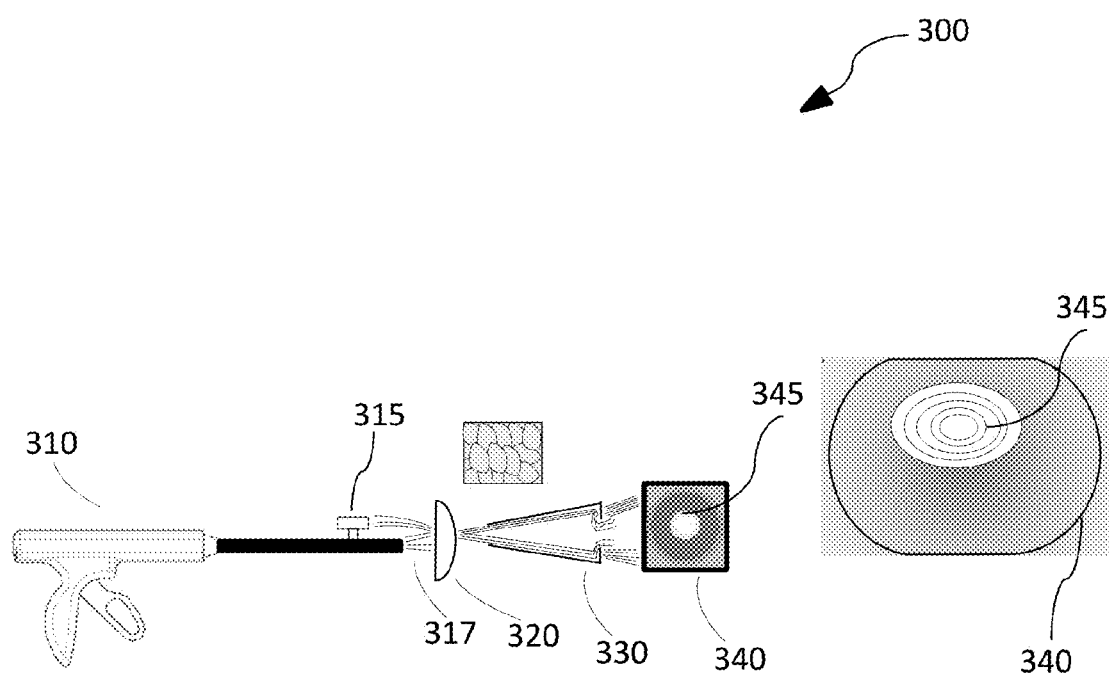
FIG. 4 is a schematic view of a pattern projection metrology system, according to an embodiment of the present disclosure.

Referring to FIG. 4, a schematic view of a pattern projection metrology system 300 is presented.

The metrology system 300 includes a surgical instrument 310 having a laser diode 315 positioned at a distal end thereof. The laser beams 317 emitted from the laser diode 315 are received by an optical diffuser 320 that diffuses two beams 330 onto, for example, an organ 340. The optical diffuser 320 further causes a light pattern 345 to be projected onto the organ 340. The light pattern 345 may be, for example, a series of concentric circles. The surgical instrument 310 may be used for laparoscopic procedures. The surgical instrument 310 is designed to satisfy certain criteria. For example, the laser diode 315 may be adapted and dimensioned to be fixedly secured to the shaft portion of the surgical instrument 310. Additionally, in a triangulation system, two or more beams may be received from different angles, which is usually achieved by keeping light sources (e.g., laser beams) apart from each other in a direction orthogonal to the axis of projection due to the small diameters of the shafts of the surgical instruments 310, as will be discussed in further detail below with reference to FIG. 5.

Figure 5:
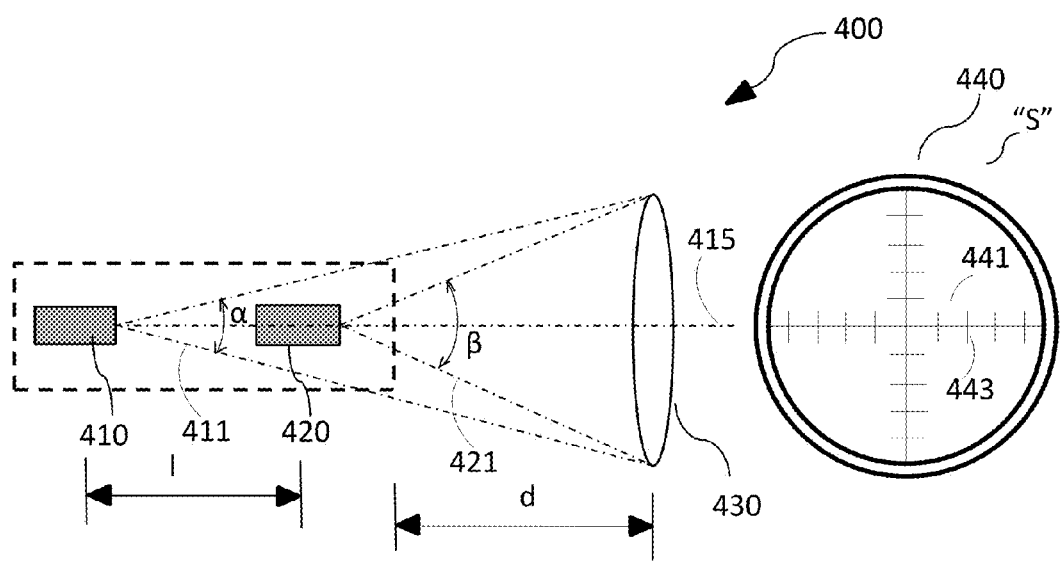
FIG. 5 is a schematic view of a projection system used in metrology with an axial location of a light source, according to an embodiment of the present disclosure.

Referring to FIG. 5, a schematic view of a projection system 400 used in metrology with an axial location of a light source is presented.

The projection system 400 includes a first light source 410 and second light source 420. The two light sources 410 and 420 are located along an axis of projection 415. Point source light emitter 410 emits a light beam 411 therefrom. Light beam 411 approximates a point at point source light emitter 410 and conically diverges from an angle of projection at an angle α. Point source light emitter 410 may be any device capable of emitting light from a narrow point, such as a laser diode or an LED. Point source light emitter 420 emits a light beam 421 therefrom. Light beam 421 approximates a point at point source light emitter 420 and conically diverges from an angle of projection at an angle β. Point source light emitter 420 may be any device capable of emitting light from a narrow point, such as a laser diode or an LED.

The second light beam 421 located at a distal end of a surgical instrument 310 (as shown in FIG. 4), has a larger angle, β, whereas the first light beam 411, located at a proximal end of a surgical instrument 310, has a smaller angle, α. As noted in FIG. 5, the light sources 410, 420 are positioned axially on the same axis 415, such that the light beams 411, 421 are coincident with the axis 415. Light beams 411, 421 are partially blocked by mask pattern or image plane 430 upon incidence with plane 430. An unblocked portion of light beams 411, 421 continues past plane 430 to reach a target site "S." The unblocked portion creates a magnified pattern 440 on target site "S." The pattern 440 may be a series of concentric circles or a cross-hair 441 with a plurality of marks 443. One skilled in the art may contemplate a plurality of different patterns to be projected having a number of different tick marks. The exemplary embodiments of the present disclosure are not limited by the shape or size of the projected patterns.

Figure 6:
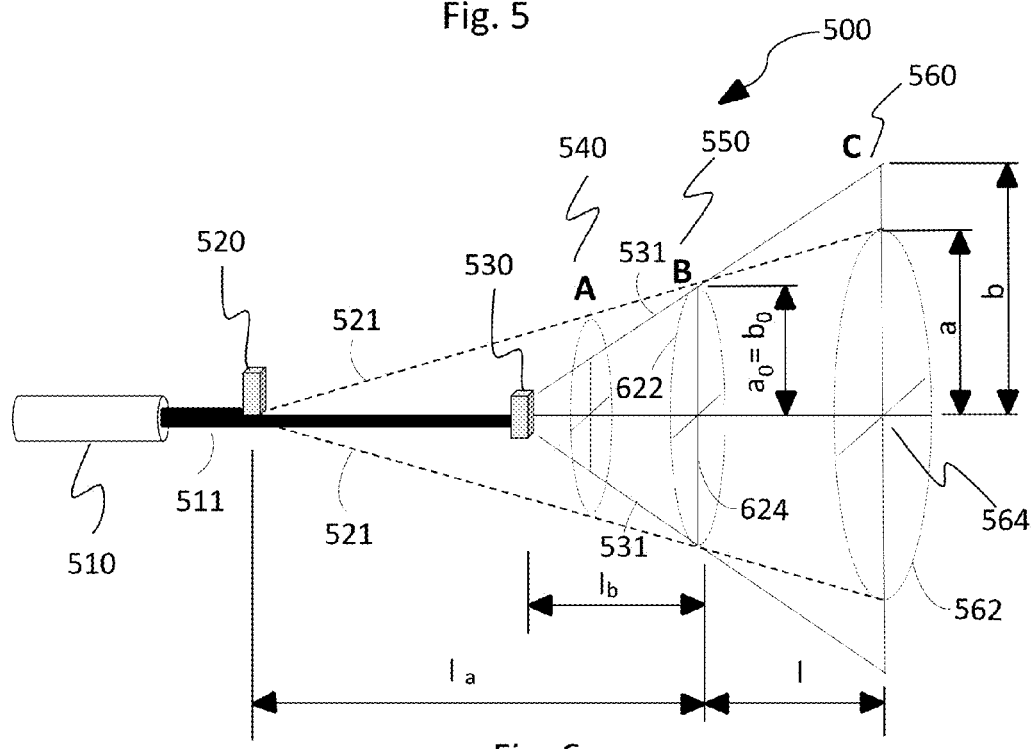
FIG. 6 is a schematic view of the optical measurement system having a laser and two diffractive elements, in accordance with another embodiment of the present disclosure.

Referring to FIG. 6, a schematic view of an optical measurement system 500 having two diffractive elements 540, 550, in accordance with an embodiment of the present disclosure is presented.

In the system 500, a point source light emitter 510 emits a light beam 511 therefrom. A first portion of light beam 511 is received by a diffractive circle pattern generator 520 located at a proximal end of, for example, a surgical instrument. A second portion of the light beam 511 is received by a diffractive cross-pattern generator 530. The light beam 521 emitted from the diffractive circle pattern generator 520 conically diverges therefrom at an angle, a. The light beam 531 emitted from the diffractive cross-pattern generator 530 conically diverges therefrom at an angle, b.

Light beam 521 is partially blocked by image plane 540 upon incidence with plane 540, whereas light beam 531 is partially blocked by at least image plane 550 upon incidence with plane 550. Unblocked portions of light beams 521, 531 continue past planes 540, 550 to reach a target site. Unblocked portions create a magnified pattern 560 on the target site. The magnified pattern 560 may include a circle 562 having an outer perimeter greater than the outer perimeters of the image planes 540, 550.

Image pattern 550 is a distance, $l_a$, from the first diffractive pattern generator 520 and a distance, l, from a target site "S" or from the third plane 560. Additionally, the image pattern 550 is a distance, $l_b$, from the second diffractive pattern generator 530. Thus, the first pattern generator 520 is located between the light source and the second pattern generator 530. This results in the first pattern generator 520 being positioned at a first distance with respect to the light source and the second pattern generator being positioned at a second distance with respect to the light source, the second distance being greater than the first distance.

Therefore, as shown in FIG. 6, the projection system includes a laser 510 and two diffractive optical elements 520, 530 having different angular divergency (a and b). The first diffuser 520 receives a portion of the laser beam 511 and the other diffuser 530 receives the remaining portion of the laser beam 511. Since angular divergences (a and b) are different, patterns are overlapped in a space in such a way that they have equal size only at a location B, on image plane 550, as depicted in FIG. 6. At longer distances, the cross pattern 624 becomes larger than the circle pattern 622, whereas at shorter distances the cross pattern 624 becomes smaller than the circle pattern 622. At location B, on image plane 550, they have the same exact size or, stated differently, they have the same pre-engineered size ($a_o=b_o$), where the patterns 562, 564 provide accurate measurements, thus allowing the system 500 to act as an accurate optical ruler. Therefore, the medical professional needs to move the surgical instrument 510 such that the circle pattern 562 and the cross pattern 564 coincide or overlap with each other in order to obtain accurate measurements of the object (e.g., an organ) to be measured. Stated differently, the end points of the cross hair align with the outer periphery of the circle for optimizing measurements of target sites, such as an organ.

In operation or use, the medical professional moves the surgical instrument 510 toward the site to be measured until both patterns 562, 564 (i.e., the circle pattern and the cross hair pattern) overlap or coincide. At the point of coincidence or overlap, the two patterns 562, 564 serve as an accurate optical ruler where tick marks 443 are equally spaced apart at predefined distances, as shown on magnified pattern 440 on target site "S" (see FIG. 5). In other words, by using such exemplary patterns, the end points of the cross hair are designed to coincide or align with the circle, thus indicating that an accurate measurement is achievable at that point.

Figure 7:
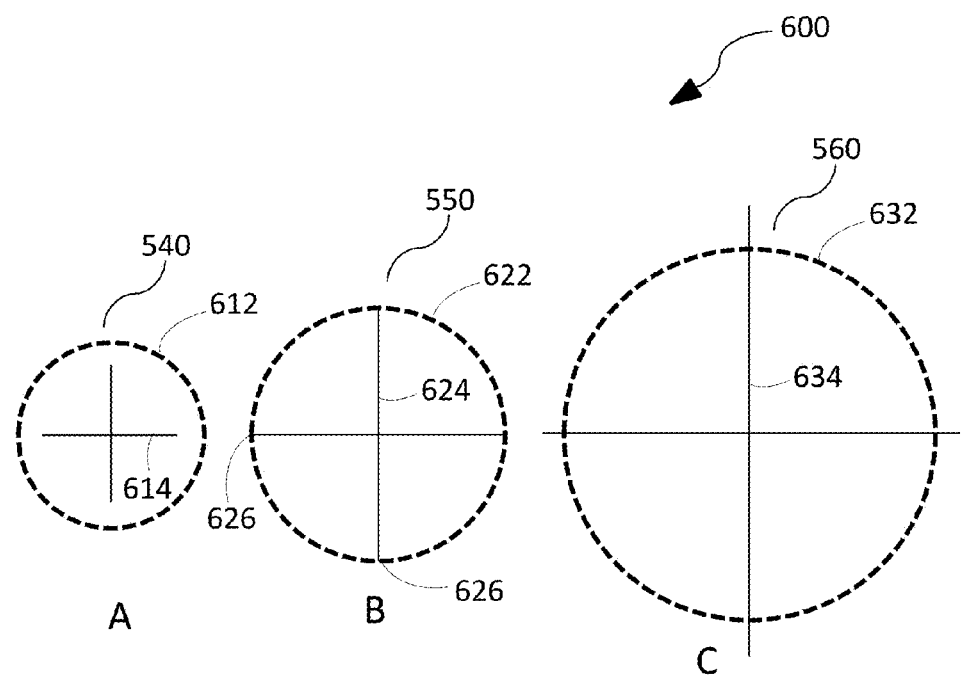
FIG. 7 is a schematic view of generated patterns based on the distance of the optical measurement system from the target site, in accordance with an embodiment of the present disclosure.

Referring to FIG. 7, a schematic view of generated patterns 600 based on the distance of the optical measurement system from the target site, in accordance with an embodiment of the present disclosure is presented.

The first pattern 540 includes a circular outer perimeter 612 and a cross hair 614. The end points of cross hair 614 do not intersect the circular outer perimeter 612. The end points of the cross hair 614 are determined by the distance of the diffractive cross-pattern generator 530 from the image plane 540, as shown in FIG. 6. At location A, an accurate measurement is not obtained since there is no overlap or coincidence of the two patterns.

The second pattern 550 includes a circular outer perimeter 622 and a cross hair 624. The end points 626 of cross hair 624 coincide with the circular outer perimeter 622. The end points 626 of the cross hair 624 are determined by the distance of the diffractive cross-pattern generator 530 from the image plane 550, as shown in FIG. 6. At location B, an accurate measurement is obtained since the two patterns coincide or are overlapped. This is the point at which accurate, real-time, in-body cavity optical metrology may be achieved. This visual indication enables a medical professional to obtain an accurate reading or measurement of a target site (e.g., an organ), via for example, tick marks placed on portions or segments of the pattern 550 (see FIG. 8).

The third pattern 560 includes a circular outer perimeter 632 and a cross hair 634. The end points of cross hair 634 intersect the circular outer perimeter 632 and extend beyond the circular outer perimeter 632. The end points of the cross hair 634 are determined by the distance of the diffractive cross-pattern generator 530 from the image plane 560, as shown in FIG. 6. At location C, an accurate measurement is not obtained since there is no overlap or coincidence of the two patterns. There is merely an intersection of the cross-hair 634 with the circle 632.

Figure 8:
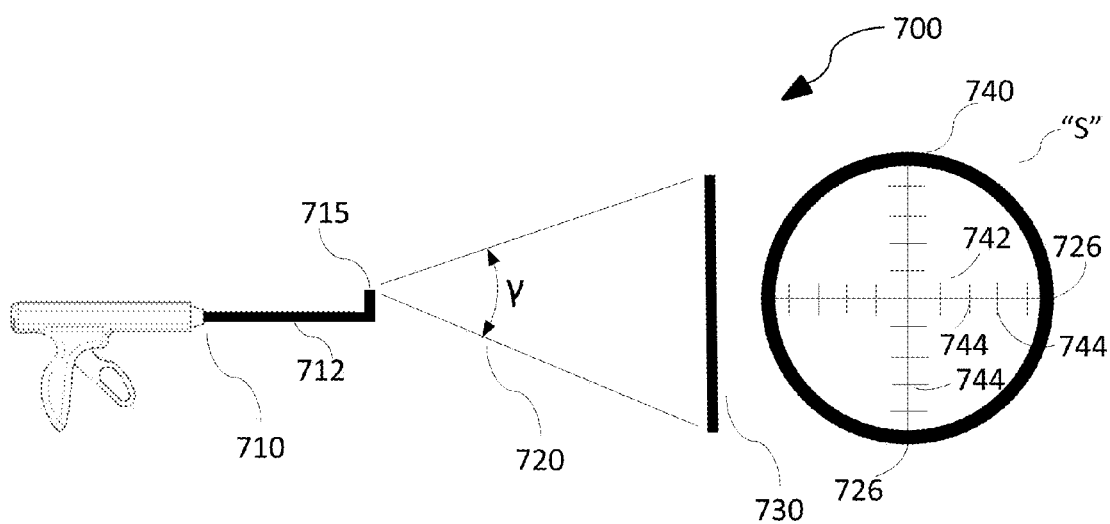
FIG. 8 is a side view of the optical measurement system mounted on a surgical instrument, in accordance with an embodiment of the present disclosure.
Figure 9:
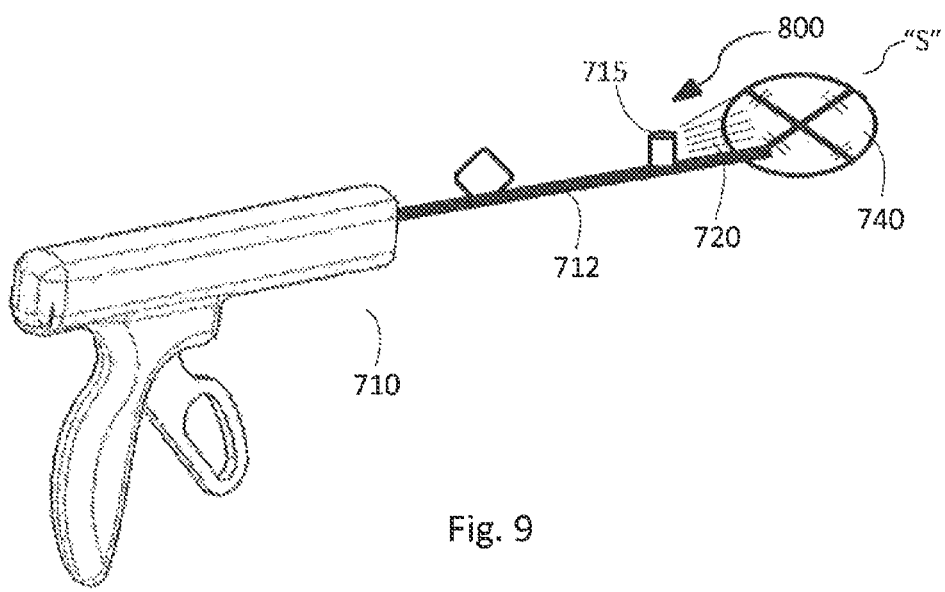
FIG. 9 is a perspective view of the optical measurement system mounted on a surgical instrument of FIG. 8, in accordance with an embodiment of the present disclosure.

Referring to FIGS. 8 and 9, side and perspective views 700, 800 of the optical measurement system 715 mounted on a surgical instrument 710, in accordance with an embodiment of the present disclosure are presented.

In FIGS. 8 and 9, a projection device 715 is mounted on a distal end of a shaft 712 of a surgical instrument 710. A light beam 720 is emitted from the projection device 715 at an angle γ. Light beam 720 is partially blocked by image plane 730 upon incidence with plane 730. Unblocked portions of the light beam 720 continue past image plane 730 and onto a target site, S, forming a pattern 740. The pattern 740 is circular in nature and includes a cross hair 742 having a plurality of marks 744. The projection device 715 acts as an optical ruler. In FIG. 8, the end points 726 of the cross hair 742 overlap or coincide with or align with the outer periphery of the circle 740. This overlap or alignment indicates or signifies that an accurate measurement may be made by the medical professional.

Figure 10:
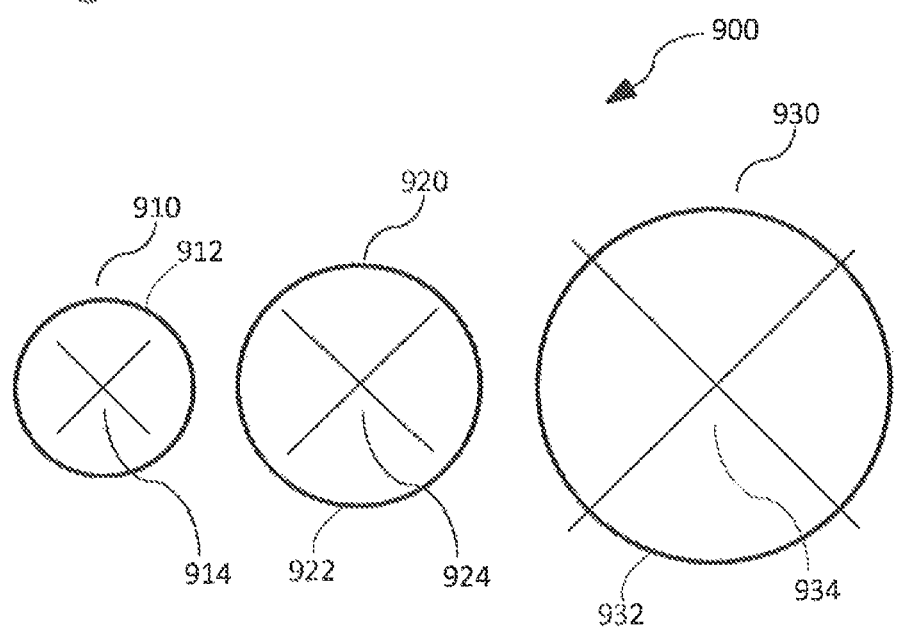
FIG. 10 is a schematic view of the projected patterns created by various locations of the surgical instruments of FIGS. 8 and 9, in accordance with an embodiment of the present disclosure.

Referring to FIG. 10, a schematic view of the projected patterns 900 created by various locations of the surgical instruments of FIGS. 8 and 9, in accordance with an embodiment of the present disclosure are presented.

The first pattern 910 includes a circular outer perimeter 912 and a cross hair 914. The end points of cross hair 914 do not intersect the circular outer perimeter 912. The end points of the cross hair 914 are determined by the distance of the diffractive cross-pattern generator 715 from the image plane 730, as shown in FIGS. 8 and 9.

The second pattern 920 includes a circular outer perimeter 922 and a cross hair 924. The end points 926 of cross hair 924 coincide or overlap or align with the circular outer perimeter 922. The end points 926 of the cross hair 924 are determined by the distance of the diffractive cross-pattern generator 715 from the image plane 730, as shown in FIGS. 8 and 9.

The third pattern 930 includes a circular outer perimeter 932 and a cross hair 934. The end points of cross hair 934 intersect the circular outer perimeter 932 and extend beyond the circular outer perimeter 932. The end points of the cross hair 934 are determined by the distance of the diffractive cross-pattern generator 715 from the image plane 730, as shown in FIGS. 8 and 9.

Figure 11:
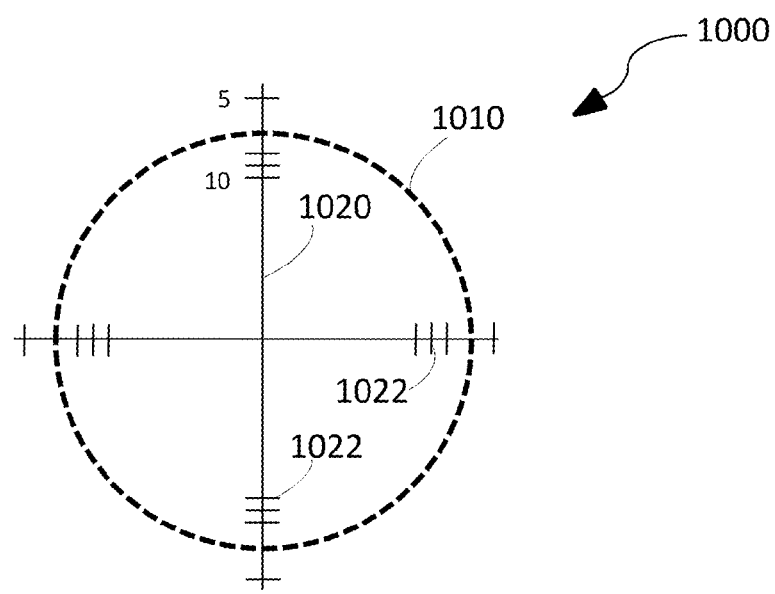
FIG. 11 is a schematic view of the cross hair depicting tick marks to provide reading of the circle diameter, in accordance with an embodiment of the present disclosure.

FIG. 11 is a schematic view 1000 of the cross hair 1020 depicting tick marks 1022 to provide reading of the circle diameter, in accordance with an embodiment of the present disclosure.

In some embodiments, it may be desirable to obtain a reading of the diameter of the circle pattern 1010 without moving the surgical instrument (see FIGS. 8 and 9). For example, a surgeon may move the surgical instrument toward the object to be measured until the circle pattern 1010 covers the entire object, at which point it may be desirable to read the diameter of the circle 1010. In the view 1000 of FIG. 11, there are two separate patterns, that is, a circle pattern 1010 and a cross hair pattern 1020. The cross hair pattern 1020 includes a plurality of tick marks 1022, which provide a reading of the circle diameter. For example, as shown in FIG. 11, a medical professional may read the circle diameter as "6," since the circle intersects a mark designating the distance as being 6 cm. It is noted that the tick marks 1022 need not be equally spaced apart. One skilled in the art may include any number of tick marks in any number of shapes or colors for providing accurate distance indications to a medical professional.

Figure 12:
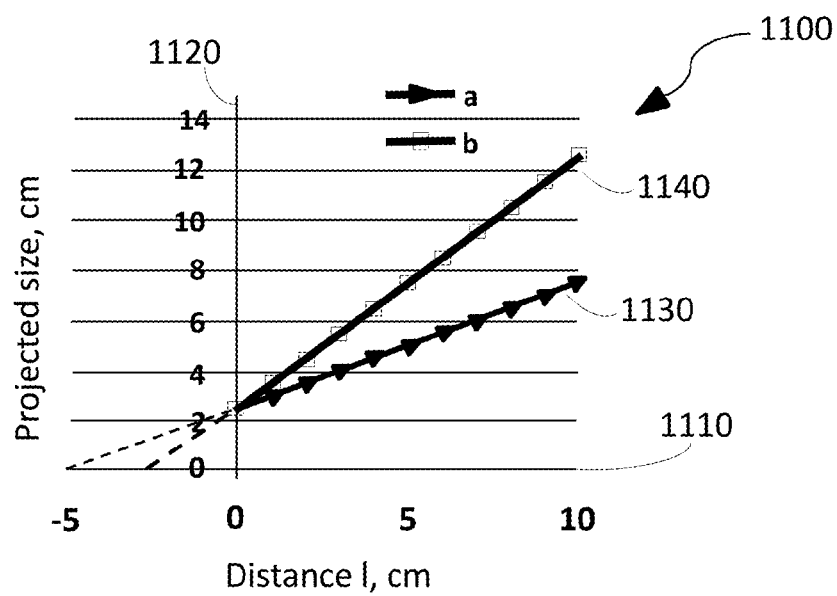
FIG. 12 is a graph illustrating pattern sizes as a function of distance of the projection system from the surgical site, in accordance with an embodiment of the present disclosure.

FIG. 12 is a graph 1100 illustrating pattern sizes as a function of the distance of the surgical instrument from the target site (e.g., an organ), in accordance with an embodiment of the present disclosure.

The graph 1100 has an x-axis 1110 representing distance and a y-axis 1120 representing projected size. Plot 1130 illustrates a first pattern size, whereas plot 1140 illustrates a second pattern size. The first and second pattern sizes 1130, 1140 may be calculated via the equations or formulas presented above with reference to FIGS. 1 and 2. For example, if it assumed that la=5 cm, lb=2.5 cm, $a_o$=$b_o$=2.5 cm, as illustrated in FIG. 7, then the projected size of the patterns 1130, 1140 may be calculated in accordance with the following formula or equation:

$$a = a_0\left(1 + \frac{l}{l_a}\right);$$

$$b = b_0\left(1 + \frac{l}{l_b}\right);$$

$$a_0 = b_0$$

Figure 13:
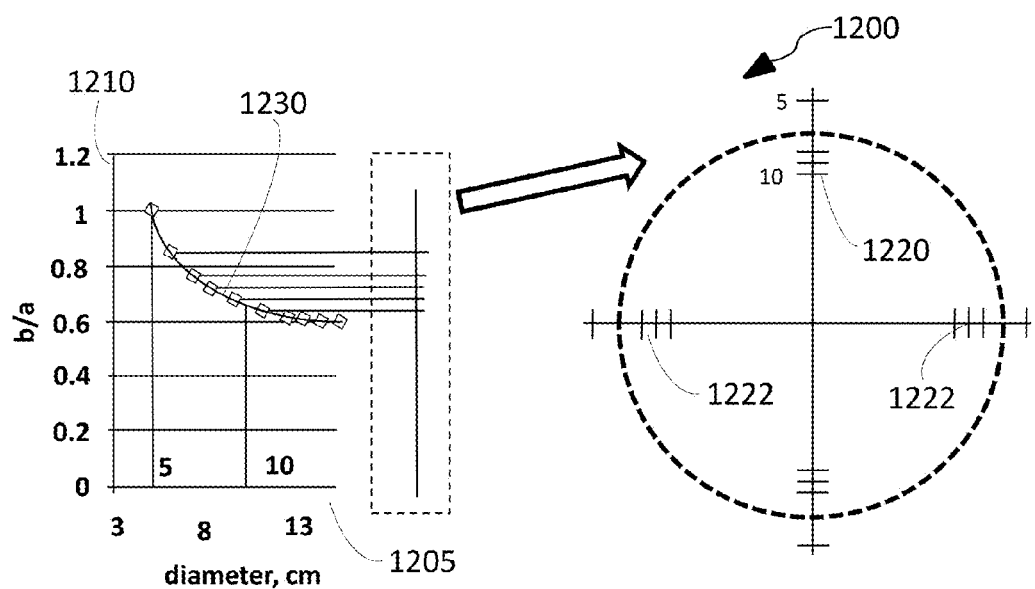
FIG. 13 provides for a calculation of a tick mark on a cross-hair pattern for reading a circle diameter, in accordance with an embodiment of the present disclosure.

FIG. 13 provides for a calculation of a tick mark 1222 on a cross-hair pattern 1220 for reading a circle diameter, in accordance with an embodiment of the present disclosure.

In FIG. 13 the x-axis 1205 represents the ratio b/a and the y-axis 1210 represents the circle diameter ($\Phi$=2*a). The line 1230 represents the change of the patterns with respect to each other as the surgical instrument is moved in and out of the surgical site. The tick marks 1222 in a cross pattern 1220 may be designed as demonstrated in FIG. 13. In the example shown, the diameter is derived to be 6 cm, thus enabling the medical professional to estimate or approximate the size of the measured structure or organ or target site with accuracy.

Figure 14:
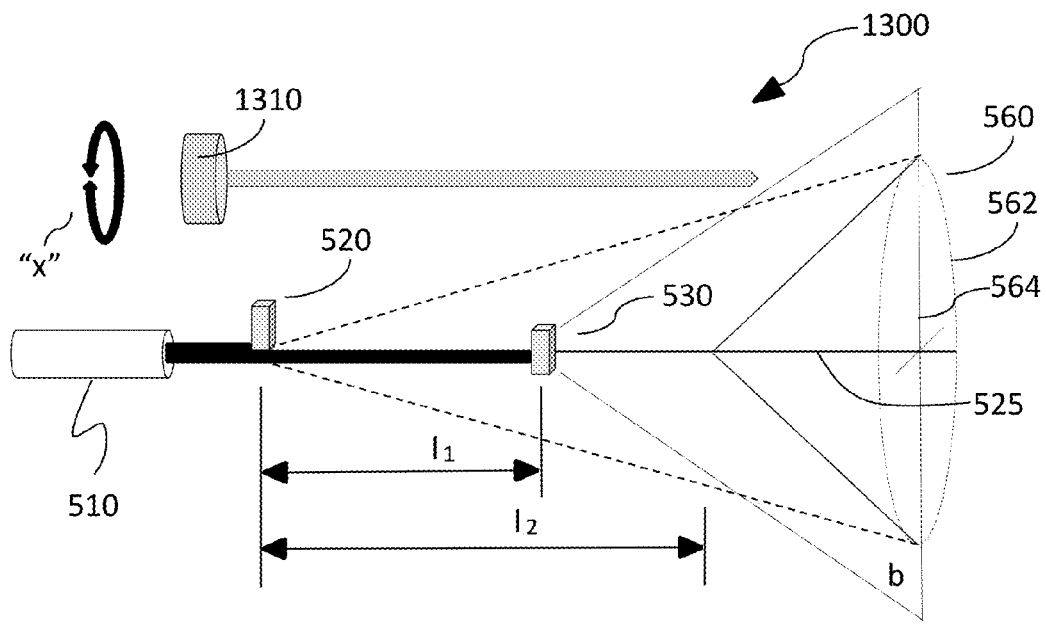
FIG. 14 is a schematic diagram of an optical measurement system having at least one moving diffractive element, in accordance with an embodiment of the present disclosure.

FIG. 14 is a schematic diagram of an optical measurement system 1300 having at least one moving diffractive element 520, 530, in accordance with an embodiment of the present disclosure.

According to FIG. 14, in some exemplary embodiments, one of the diffractive elements 520, 530 may have translational motion along the laser axis 525. At a given position of the instrument 510, rotation of the knob 1310 at the proximal end of the surgical instrument 510, causes a change in size of the projected patterns 562, 564. The knob 1310 should be rotated until both patterns 562, 564 have the same size or coincide or overlap. For example, if it assumed that the diameter of the circle pattern 562 at the site of projection is, $\Phi$, and the second diffuser 530 is at distance, $l_1$, then at this distance the projected cross pattern 564 has a size, b, and is larger than the circle diameter 562. By rotating the knob 1310, in the direction "x," the medical professional may achieve an equal size of the two patterns 562, 564 (i.e., b=$\Phi$) at the location of the second diffuser 530 at distance, $l_2$. Since the size of the cross pattern 564, b, is proportional to the distance between the diffuser 530 and the target site 560, the knob 1310 may be calibrated in units of circle diameter. Thus, the reading of the knob's scale provides a desired value for the circle diameter. Additionally, the motion or movement of one of the elements 520, 530 is associated with a change of the size of the projected patterns 562, 564. Thus, a direct relationship is established between the size of the projected pattern and the distance of the surgical instrument/projection system from the target site.

One advantage of the present disclosure is to create a small form factor, inexpensive projection device for real-time, in-body cavity optical metrology, in order to reduce overall surgery time and cognitive burden on a surgeon, as well as potentially improve patient outcomes with more accurate and smaller incision procedures, which are less prone to human errors or miscalculations.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A system for performing optical measurements, the system comprising:
    a light source configured to emit a light beam;
    a first pattern generator defining a longitudinal axis and configured to project a first generated pattern, the first pattern generator configured to receive a portion of the light beam; and
    a second pattern generator placed along the longitudinal axis defined by the first pattern generator and configured to project a second generated pattern, the second pattern generator longitudinally spaced from the first pattern generator to define a gap therebetween, and the second pattern generator configured to receive a remaining portion of the light beam;
    wherein the first and second generated patterns have different angular divergency.

2. The system according to claim 1, wherein the light source is a laser.

3. The system according to claim 1, wherein the first pattern generator is a diffractive circle pattern generator, whereas the second pattern generator is a diffractive cross pattern generator.

4. The system according to claim 1, wherein the first pattern generator is located between the light source and the second pattern generator.

5. The system according to claim 1, wherein the first pattern generator is positioned at a first distance with respect to the light source and the second pattern generator is positioned at a second distance with respect to the light source, the second distance being greater than the first distance.

6. The system according to claim 1, wherein the first and second generated patterns are projected onto a target site in an overlapping manner.

7. The system according to claim 6, wherein the first generated pattern is a circle and the second generated pattern is a cross-hair that is adjusted with respect to the circle based on the distance of the system relative to the target site.

8. The system according to claim 1, wherein adjustment of the first and second generated patterns with respect to each other cause the system to serve as an optical ruler for performing the optical measurements when the first and second generated patterns overlap.

9. The system according to claim 1, wherein the light source is coaxial with one of the first or second pattern generators.

10. The system according to claim 1, wherein the system is mounted on a surgical device.

11. The system according to claim 1, wherein the second generated pattern is a diffractive cross pattern having a plurality of tick marks thereon configured to provide a positional relationship with the first generated pattern.

12. The system according to claim 1, wherein at least one of the first and second pattern generators is a moving diffractive element.

13. The system according to claim 12, wherein the moving diffractive element is a lead screw translational motion mechanism.

14. A surgical instrument comprising:
a handle portion;
a body portion extending distally from the handle portion and defining a longitudinal axis;
an end effector assembly disposed at a distal end of the body portion; and
an optical measurement system including:
a beam delivery element for projecting a beam along an illumination path and onto a plane; and
first and second diffractive optical elements positioned along the illumination path of the beam delivery element, the first and second diffractive optical elements configured to project first and second generated patterns, in an overlapping manner, onto the plane, and having different angular divergency, the first diffractive optical element being separate from the second diffractive optical element, and the first diffractive optical element configured to receive a portion of the beam.

15. The surgical instrument according to claim 14, wherein the beam delivery element is a laser.

16. The surgical instrument according to claim 14, wherein the first diffractive optical element is a diffractive circle pattern generator and the second diffractive optical element is a diffractive cross pattern generator.

17. The surgical instrument according to claim 14, the first diffractive optical element is located between the beam delivery element and the second diffractive optical element.

18. The surgical instrument according to claim 14, wherein the first diffractive optical element is positioned at a first distance with respect to the beam delivery element and the second pattern diffractive optical element is positioned at a second distance with respect to the beam delivery element, the second distance being greater than the first distance.

19. The surgical instrument according to claim 14, wherein the first generated pattern is a circle and the second generated pattern is a cross-hair that is adjusted with respect to the circle based on the distance of the optical measurement system relative to a target site.

20. The surgical instrument according to claim 14, wherein adjustment of the first and second generated patterns with respect to each other cause the optical measurement system to serve as an optical ruler for performing optical measurements when the first and second generated patterns overlap.

21. The surgical instrument according to claim 14, wherein the second generated pattern is a diffractive cross pattern having a plurality of tick marks thereon configured to provide a positional relationship with the first generated pattern.

22. The surgical instrument according to claim 14, wherein at least one of the first and second diffractive optical elements is a moving diffractive element.

23. The surgical instrument according to claim 22, wherein the moving diffractive element is a lead screw translational motion mechanism.

24. A method of performing optical measurements, the method comprising:
mounting an optical measurement system onto a surgical instrument;
projecting a beam along an illumination path and onto a plane, via a beam delivery element;
positioning first and second diffractive optical elements along the illumination path, the first and second diffractive optical elements longitudinally spaced apart such that the first diffractive optical element receives a portion of the beam; and
projecting first and second generated patterns, in an overlapping manner, onto the plane, and having different angular divergency, via the first and second diffractive optical elements.

25. The method according to claim 24, wherein the first generated pattern is a circle and the second generated pattern is a cross-hair that is adjusted with respect to the circle based on the distance of the optical measurement system relative to a target site.

26. The method according to claim 24, wherein adjustment of the first and second generated patterns with respect to each other cause the optical measurement system to serve as an optical ruler for performing optical measurements when the first and second generated patterns overlap.

27. The method according to claim 24, wherein the second generated pattern is a diffractive cross pattern having a plurality of tick marks thereon configured to provide a positional relationship with the first generated pattern.

28. The method according to claim 24, wherein at least one of the first and second diffractive optical elements is a moving diffractive element.

29. The method according to claim 28, wherein the moving diffractive element is a lead screw translational motion mechanism.

* * * * *